Figure 1:
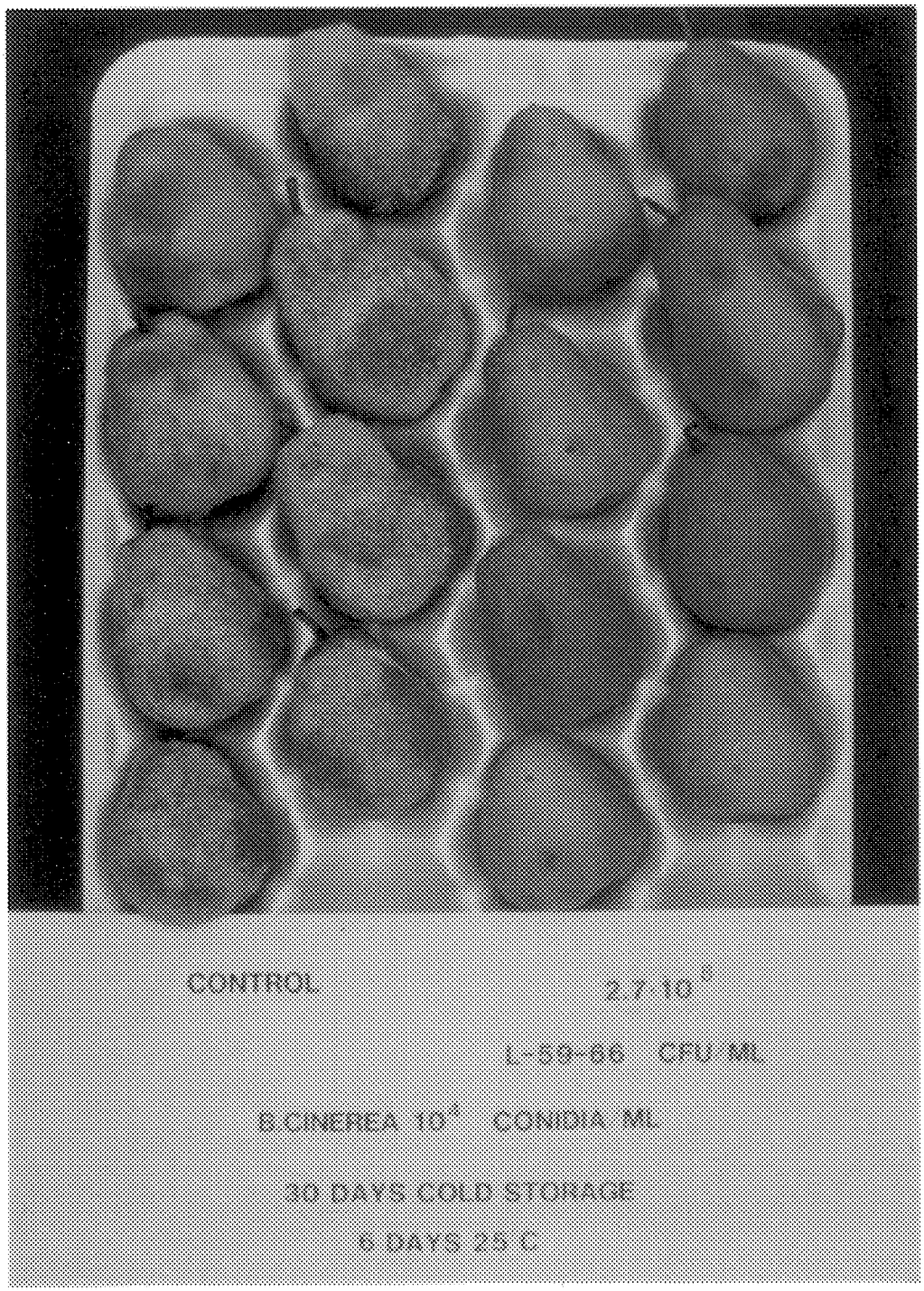
Figure 2:
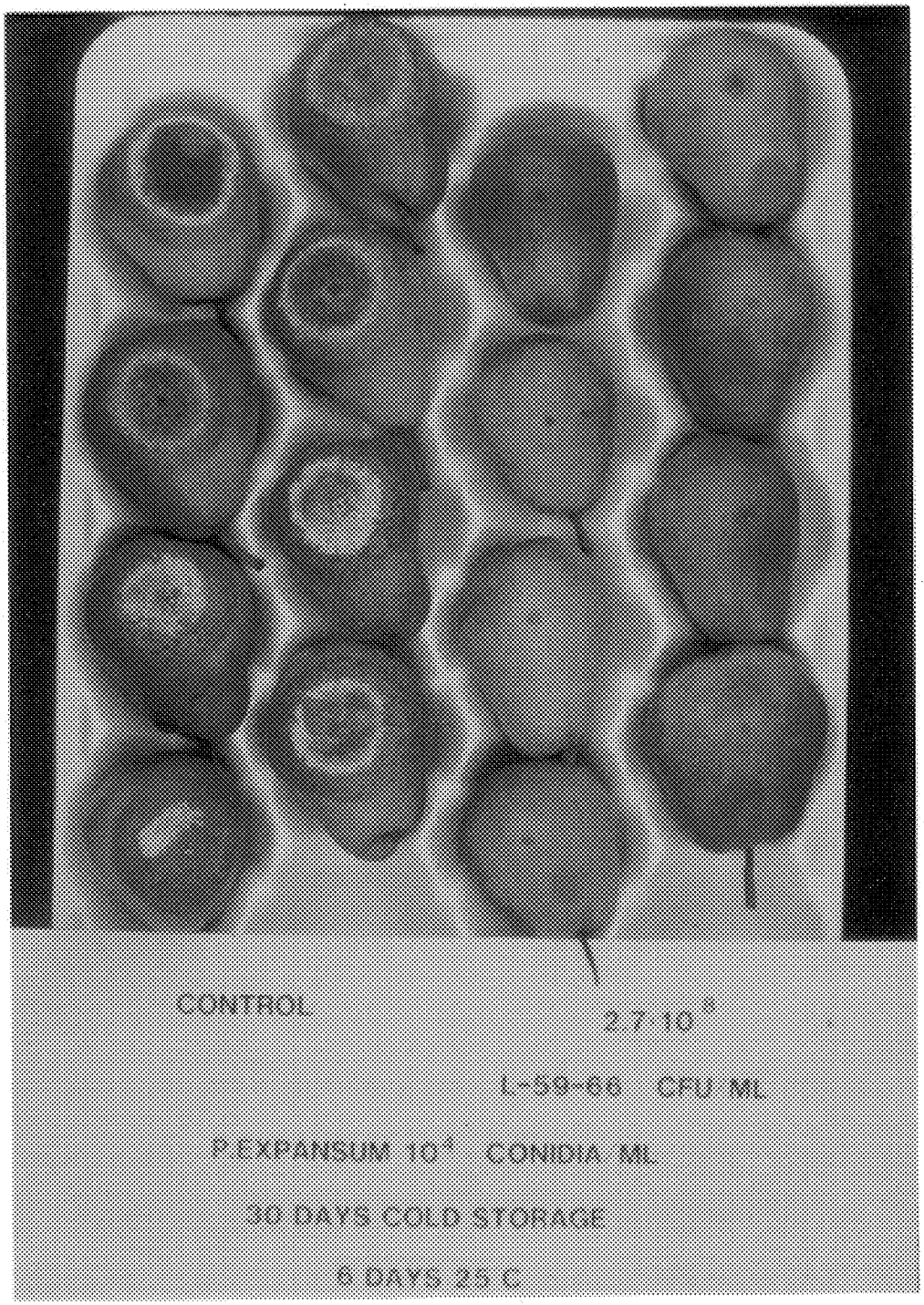

United States Patent [19]
Janisiewicz et al.

[11] Patent Number: 6,017,752
[45] Date of Patent: Jan. 25, 2000

[54] BIOLOGICAL CONTROL OF POSTHARVEST DISEASES OF POME FRUIT WITH *PSEUDOMONAS SYRINGAE* PV. *LACHRYMANS*

[75] Inventors: Wojciech J Janisiewicz, Frederick, Md.; Leonard Yourman, Washington, D.C.

[73] Assignee: The United States of America as represented by the Secretary of Agriculture, Washington, D.C.

[21] Appl. No.: 07/618,437

[22] Filed: Nov. 27, 1990

[51] Int. Cl.[7] .................................................. C07G 17/00
[52] U.S. Cl. ................ 435/267; 435/252.34; 435/253.3; 435/262; 435/874
[58] Field of Search ..................................... 435/874, 262, 435/267, 252.34, 253.3, 243, 252.1; 71/6

[56] References Cited

PUBLICATIONS

Janisiewicz, W.J., "Biological Control of Diseases of Fruit," in K. J. Mukerji, and K. L. Gary (Ed.), *Biocontrol of Plant Diseases*, CRC Press, Boca Raton, pp. 153–165 (1988).

Janisiewicz, W.J., "Postharvest Biological Control of Blue Mold on Apples," *Phytopathology*, vol. 77(3), pp. 481–485 (1987).

Janisiewicz et al. "Biocontrol of Blue Mold . . ." Phytopathology vol. 80 No. 7 Jul. 1990 pp. 670–1, (From A PS Meeting of Mar. 1990).

Janisiewicz et al "Biocontrol of Post Harvest Disease . . ." Biosis Abstract 88:242666 of Phytopathology 78(2) 1988.

Janisiewicz, W. "Biological Control of Postharvest Diseases of Pears with *Pseudomonas syringae* pv *Lachrymans*" Phytopathology, vol. 79, No. 10 (Oct. 1989).

Biosis Abstract 90:123865 "Biological Control of Postharvest Diseases of Pears . . ." Janisiewicz, W. from Ann. Meeting of Amer. Phytopath. Soc. (Aug. 20, 1989).

Takeda, F et al. "Fruit Rot Control in Small Fruit Crops . . ." Hort Science, vol. 25, No. 6 (Jun., 1990).

Takeda, F et al. "Pyrrolnitrin Delays PostHarvest Fruit Rot" Hort Science, vol. 25, No. 3 (Mar., 1990).

*Primary Examiner*—Leslie Wong
*Attorney, Agent, or Firm*—M. Howard Silverstein; John D. Fado; Janelle S. Graeter

[57] ABSTRACT

An isolate from the surface of apple leaves, *Pseudomonas syringae* pv. *lachrymans* having the deposited accession number NRRL B-18739, exhibits antifungal properties. The organisms have utility in methods for controlling postharvest disease in agricultural commodities caused by fungal pathogens.

2 Claims, 6 Drawing Sheets

BIOLOGICAL CONTROL OF POSTHARVEST DISEASES OF POME FRUIT WITH *PSEUDOMONAS SYRINGAE* PV. *LACHRYMANS*

BACKGROUND OF THE INVENTION

1. Field of the Invention

The present invention relates to the biological control of postharvest diseases in fruits. More particularly, this invention relates to the use of *Pseudomonas syringae* pv. *lachrymans* to biologically control blue-mold caused by *Penicillium expansum* and grey-mold caused by *Botrytis cinerea.*

2. Description of the Prior Art

Postharvest diseaes of fruit cause 15 to 25% losses yearly in the fruit industry worldwide. Fungicides, the major weapon in combatting these diseases, are often ineffective and pose hazards to humans and the environment. Therefore, a critical need exists for new methods to control postharvest diseases.

Recently, it has been shown that the postharvest treatment of fruit with antagonistic microorganisms is an effective approach to the control of postharvest rots. Remarkable success was shown in the control of brown rot in peaches caused by *Monilinia fructicola* (Wint.) Honey with *Bacillium subtilis*. Pusey et al. (Plant Dis. 86: 753–756 (1986)). De Matos was able to reduce mold incidence from 35% to 8% when a species of Trichoderma was inoculated with *Penicillium digitatum* into lemon peel. De Matos, Ph.D. Dissertation, University of California, Riverdale, (1983). Singh and Deverall demonstrated biocontrol with bacterial antagonists to the citrus pathogens *Alternaria citri* Pierce, *Geotrichum candidum* link. ex Pers., and *P. digitatum*. Singh et al. (Trans. Br. Mycol. Soc. 83: 487–490 (1983)). Dipping wounded citrus fruit in suspensions of bacterial cells, particularly a strain of *Bacillus subtilis* (Ehrenber) Cohn, delayed decay by the three rot pathogens.

*Trichoderma viride* Pers. & S. F. Gray applied to strawberry plants in the field was shown to partially control grey-mold on strawberry fruits after harvest. Tronsmo et al. (Neth. J. Plant Pathol. 83 (suppl. 1): 449–455 (1977)). Also, partial control of rot in apples caused by *B. cinerea* flower infection was obtained by applying conidia *T. harzianium* Rifai to apple trees during bloom. Control was comparable to prior known fungicidal treatments. Tronsmo et al. (Plant Dis. 64: 1009 (1980)).

*P. cepacia* has been reported to reduced southern maize leaf blight caused by *Bipolaris maydis* in greenhouse tests, Sleesman et al. (Phytopathology 66: 1214–1218 (1976)), decrease peanuts Cerospora leaf spot and tobacco Alternaria leaf spot in the field, Spur (Phytopathology News (Abstract) 74:17 (1978)), and to control damping off of onion seedlings by *Fusarium oxysporum* f.sp. *cepae*. Kawamoto et al. (Plant Dis. Rep. 60: 189–191 (1976)).

SUMMARY OF THE INVENTION

Certain strains of *Pseudomonas syringae* pv. *lachrymans* have been isolated from apple leaves and found to exhibit inhibitory activity against major postharvest pathogens. These strains are used effectively to control postharvest rots in Pome fruits. Fruit dipped in aqueous solutions of *P. syringae* pv. *lachrymans* provide excellent protection against *Penicillium expansum* and Botrytis cinerea at ambient room temperature as well as those temperatures used under cold storage conditions.

A viable culture of *Pseudomonas syringae* pv. *lachrymans* useful in the context of the present invention was deposited on Nov. 5, 1990 with the culture collection at the Northern Regional Research Center, U.S. Department of Agriculture, Peoria, Ill. 61604, pursuant to the provisions of the Budapest Treaty on the International Recognition of the Deposit of Microorganisms for the Purposes of Patent Procedure and accorded the acquisition number NRRL B-18739.

Accordingly, it is an object of the present invention to provide biocontrol agents that are safe and highly effective at controlling a number of postharvest diseases.

BRIEF DESCRIPTION OF THE DRAWINGS

FIG. 1 Shows the control of grey-mold on "Red Bartlett" pears with *Pseudomonas syringae* pv. *lachrymans.* Protetion of the fruit is continuous. No new lesions developed after 30 days of cold storage at 2° C. and subsequent incubation for 6 days at 25° C.

FIG. 2 Shows the control of blue-mold on "Red Barlett" pears with *Pseudomonas syringae* pv. *lachrymans.* Protection of the fruit is continuous. No new lesions developed after 30 days of cold storage at 2° C. and subsequent incubation for 6 days at 25° C.

FIG. 3 Shows the lesion diameter (mm) for *P. expansum* for fruit stored at 1° C. for 30 days.

FIG. 4 Shows the lesion diameter (mm) for *B. cinerea* for fruit stored at 1° C. for 30 days.

FIG. 5 Shows the lesion diameter (mm) for *P. expansum* for fruit stored at 18° C. for 7 days.

FIG. 6 Shows the lesion diameter (mm) for *B. cinerea* for fruit stored at 18° C. for 7 days.

DETAILED DESCRIPTION OF THE INVENTION

Strain L-59-66 (K-1) of *Pseudomonas syringae* pv. *lachrymans* (NRRL B-18739) was isolated from apple leaves by washing leaves with phosphate buffer and plating the washing on nutrient yeast dextrose agar (NYDA) media. This strain was selected out of a few hundred various bacterial and yeast isolates which were screened on apples for inhibitory activity against major postharvest pathogens.

EXAMPLE 1

Screening Procedure

After colonies were aroused on NYDA plates seeded with leaf washing, the individual colonies were transferred and purified. They were then grown on NYDA slants for 24–48 hours and three transfer loops of the bacterium were suspended in 5 ml of water. Washed 'Golden Delicious' apples were wounded 3 mm deep and 3 mm wide and were inoculated with 20 $\mu$l of the microbial suspension. This was followed by inoculation with 20 $\mu$l of the pathogen spore suspension at a concentration of $1\times10^4$ conidia/ml. After 6 days incubation at 24° C., the diameter of the lesions (rots) originating from the wounds was measured. Apples protected with the strain L-59-66 (NRRL B-18739) did not develop any lesions. During secondary screening, inoculation was conducted in a similar fashion except that three concentrations of the antagonist were used: $3\times10^7$, $1.7\times10^8$, and $5.4\times10^8$ CFU/ml and tests were conducted on apples and 'Red Bartlett' pears. The fruit was stored at 24° C. for six days and at 2° C. for 30 days. No lesions developed on any apple or pear protected with the antagonist and inoculated with *P. expansum* and *B. cinerea* spores.

Large scale tests were conducted on 'Red Bartlett' pears and 'Golden Delicious' apples wounded with two nails protruding from a block of wood. The nail wounds imitate the most commonly encountered wounds on fruit caused by stem damage. The wounded fruit were placed in a plastic bucket and dipped in a tank containing 10–12 liters of suspension of the antagonist and pathogen conidia. Three concentrations of the antagonist were used $2.2\times10^8$, $3.2\times10^8$, and $5.4\times10^8$ CFU/ml. The conidia concentrations of the pathogens were always $1\times10^4$ conidia/ml. One half of the treated fruit was stored at 24° C. and the other half at 2° C. The fruit stored at 24° C. was evaluated for rot development after six days and the fruit stored at 2° C. after 30 days. There were 15 fruit per replicate and three replicates per treatment. Thus, 90 wounds were evaluated in each treatment. Excellent control was obtained in all treatments. In the case of *B. cinerea* inoculation (Tables 1 and 2), no lesion developed on pears treated with $5.4\times10^8$ CFU/ml and apples with $2.2\times10^8$ CFU/ml and stored at 24° C. At 2° C. storage, no lesion developed on apples at $5.4\times10^8$ CFU/ml and the average lesion on pears at this concentration was 0.3 mm.

TABLE 1

Lesion Development on Wounded Red Bartlett Pears Dipped (2 min.) in a Suspension of *Botrytis cinerea* ($1 \times 10^4$ conidia/ml) and *Pseudomonas syringae* pv. *lachrymans*

| | STORAGE TEMPERATURE | | | |
|---|---|---|---|---|
| | 2° C. | | 24° C. | |
| P.s. lachrymans ($\times 10^8$ CFU/ml) | lesion dia$^x$ (mm) | % infect. | lesion dia$^x$ (mm) | % infect. |
| 0.0 | 30.7 ± 8.5 | 86 | 37.0 ± 3.6 | 100 |
| 2.2 | 6.5 ± 3.0 | 29 | 4.0 ± 4.4 | 22 |
| 3.2 | 1.8 ± 0.3 | 12 | 0.3 ± 0.3 | 2 |
| 5.4 | 1.0 ± 0.5 | 7 | 0.0 ± 0.0 | 0 |

$^x$Average lesion diameter of 90 wounds (15 fruit/rep, 2 wounds/fruit, 3 rep/treatment)

TABLE 2

Lesion Development on Wounded Golden Delicious Apples Dipped (2 min.) in a Suspension of *Botrytis cinerea* ($1 \times 10^4$ conidia/ml) and *Pseudomonas syringae* pv. *lachrymans*

| | STORAGE TEMPERATURE | | | |
|---|---|---|---|---|
| | 2° C. | | 24° C. | |
| P.s. lachrymans ($\times 10^8$ CFU/ml) | lesion dia$^x$ (mm) | % infect. | lesion dia$^x$ (mm) | % infect. |
| 0.0 | 54.3 ± 2.1 | 100 | 54.3 ± 1.5 | 100 |
| 2.2 | 1.0 ± 1.0 | 6 | 0.9 ± 0.8 | 3 |

TABLE 2-continued

Lesion Development on Wounded Golden Delicious Apples Dipped (2 min.) in a Suspension of *Botrytis cinerea* ($1 \times 10^4$ conidia/ml) and *Pseudomonas syringae* pv. *lachrymans*

| | STORAGE TEMPERATURE | | | |
|---|---|---|---|---|
| | 2° C. | | 24° C. | |
| P.s. lachrymans ($\times 10^8$ CFU/ml) | lesion dia$^x$ (mm) | % infect. | lesion dia$^x$ (mm) | % infect. |
| 3.2 | 2.3 ± 1.5 | 9 | 0.4 ± 0.7 | 2 |
| 5.4 | 0.3 ± 0.6 | 3 | 0.0 ± 0.0 | 0 |

$^x$Average lesion diameter of 90 wounds (15 fruit/rep, 2 wounds/fruit, 3 rep/treatment)

With *P. expansum* (Tables 3 and 4), no lesion developed with any concentrates tested on pears at 24° C., the average lesion on apples was 10 mm. However, at 2° C., the average lesion on apples was only 1.0 mm. The protection is ongoing, since fruit removed from cold storage to room temperature did not develop any new lesions. Results from these tests indicate that the antagonist provides excellent protection of severely wounded fruit against *P. expansum* and *B. cinerea* at room temperature and under cold storage conditions.

TABLE 3

Lesion Development on Wounded Red Bartlett Pears Dipped (2 min.) in a Suspension of *Penicillium expansum* ($1 \times 10^4$ conidia/ml) and *Pseudomonas syringae* pv. *lachrymans*

| | STORAGE TEMPERATURE | | | |
|---|---|---|---|---|
| P.s. lachrymans | 2° C. | | 24° C. | |
| ($\times 10^8$ CFU/ml) | lesion dia$^{xy}$ | % infect. | lesion dia$^z$ | % infect. |
| 0.0 | 21.1 ± 3.7 | 97 | 22.0 ± 2.0 | 100 |
| 2.2 | — | — | 0.0 ± 0.0 | 0 |
| 2.7 | 0.0 ± 0.0 | 0 | — | — |
| 3.2 | — | — | 0.0 ± 0.0 | 0 |
| 5.4 | — | — | 0.0 ± 0.0 | 0 |

$^x$Cut wounds
$^y$Average lesion diameter of 30 wounds (10 fruit/rep, 1 wound/fruit, 3 rep/treatment).
$^z$Average lesion diameter of 90 wounds (15 fruit/rep, 2 wounds/fruit, 3 rep/treatment)

TABLE 4

Lesion Development on Wounded Golden Delicious Apples Dipped (2 min.) in a Suspension of *Penicillium expansum* ($1 \times 10^4$ conidia/ml) and *Pseudomonas syringae* pv. *lachrymans*

| | STORAGE TEMPERATURE | | | |
|---|---|---|---|---|
| | 2° C. | | 24° C. | |
| P.s. lachrymans ($\times 10^8$ CFU/ml) | lesion dia$^x$ (mm) | % infect. | lesion dia$^x$ (mm) | % infect. |
| 0.0 | 25.0 ± 2.6 | 83 | 38.0 ± 1.0 | 100 |
| 2.2 | 0.0 ± 0.0 | 0 | 14.0 ± 3.0 | 64 |
| 3.2 | 2.0 ± 2.0 | 10 | 11.7 ± 3.2 | 61 |
| 5.4 | 1.4 ± 1.0 | 9 | 10.3 ± 0.6 | 57 |

$^x$Average lesion diameter of 90 wounds (15 fruit/rep, 2 wounds/fruit, 3 rep/treatment)

EXAMPLE 2

Large Scale Dip Testing

Analysis of antagonistic effect for *Penicillium expansum* and *Botyris cinerea* were performed using strains of *P. syringae* pv. *lachrymans*. The method employed was that essentially described in example 1 with the exception of the age of the fruit as well as the storage conditions.

Four pear cultivars were used, Anjou, Bartlett, Bosc and Red Bartlett. The fruit were wounded either with a sharp instrument to produce a "cut" or a nail to produce a "puncture" wound. The effectiveness of *P. syringae* as a biocontrol agent was accessed under large scale conditions to imitate those of commercial storage facilities:

1 bushel box=4 trays/box=15 fruit/tray.

At least 1 bushel box/cutivar tested was prepared for each experiment.

Figure 3:
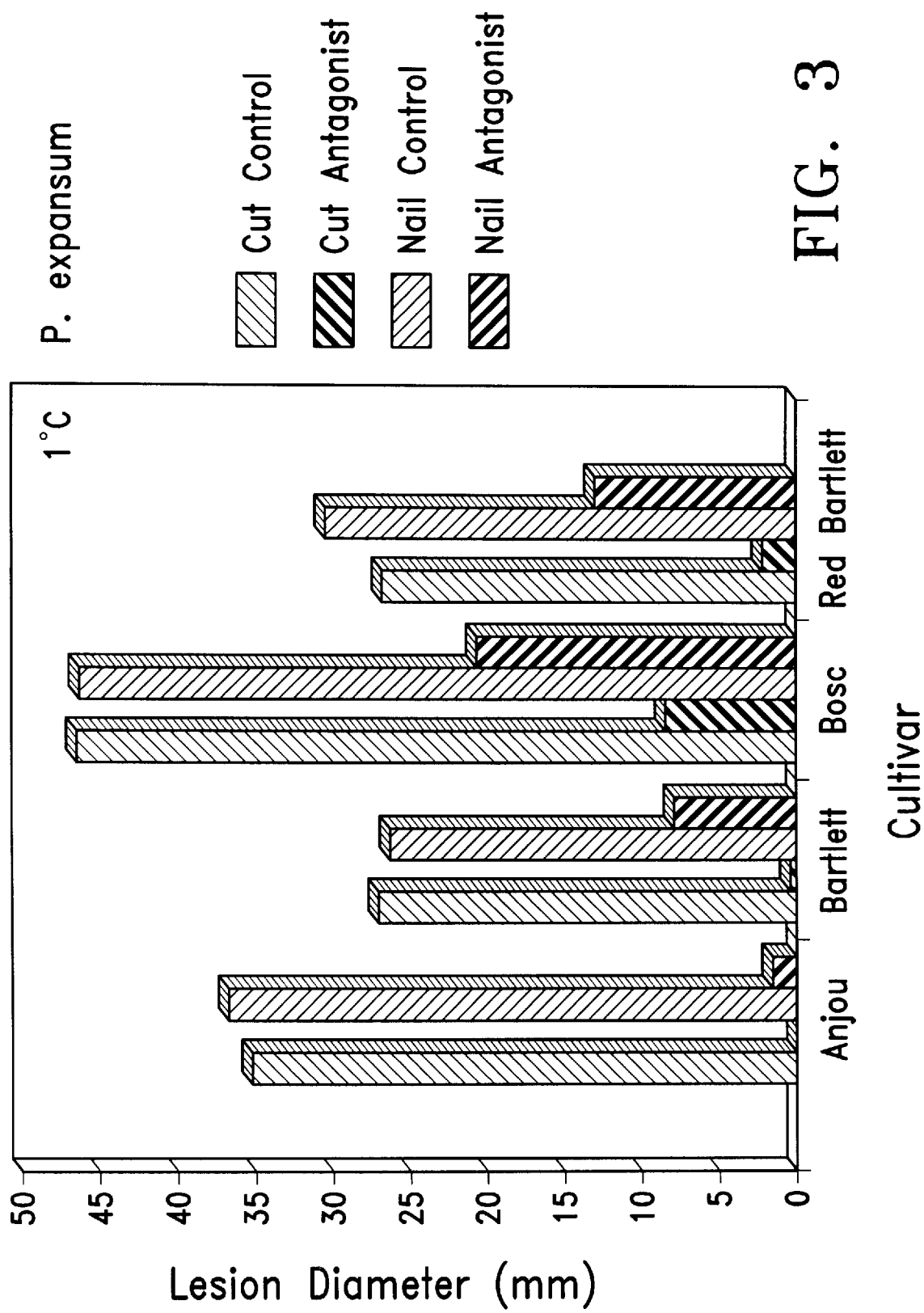
Figure 4:
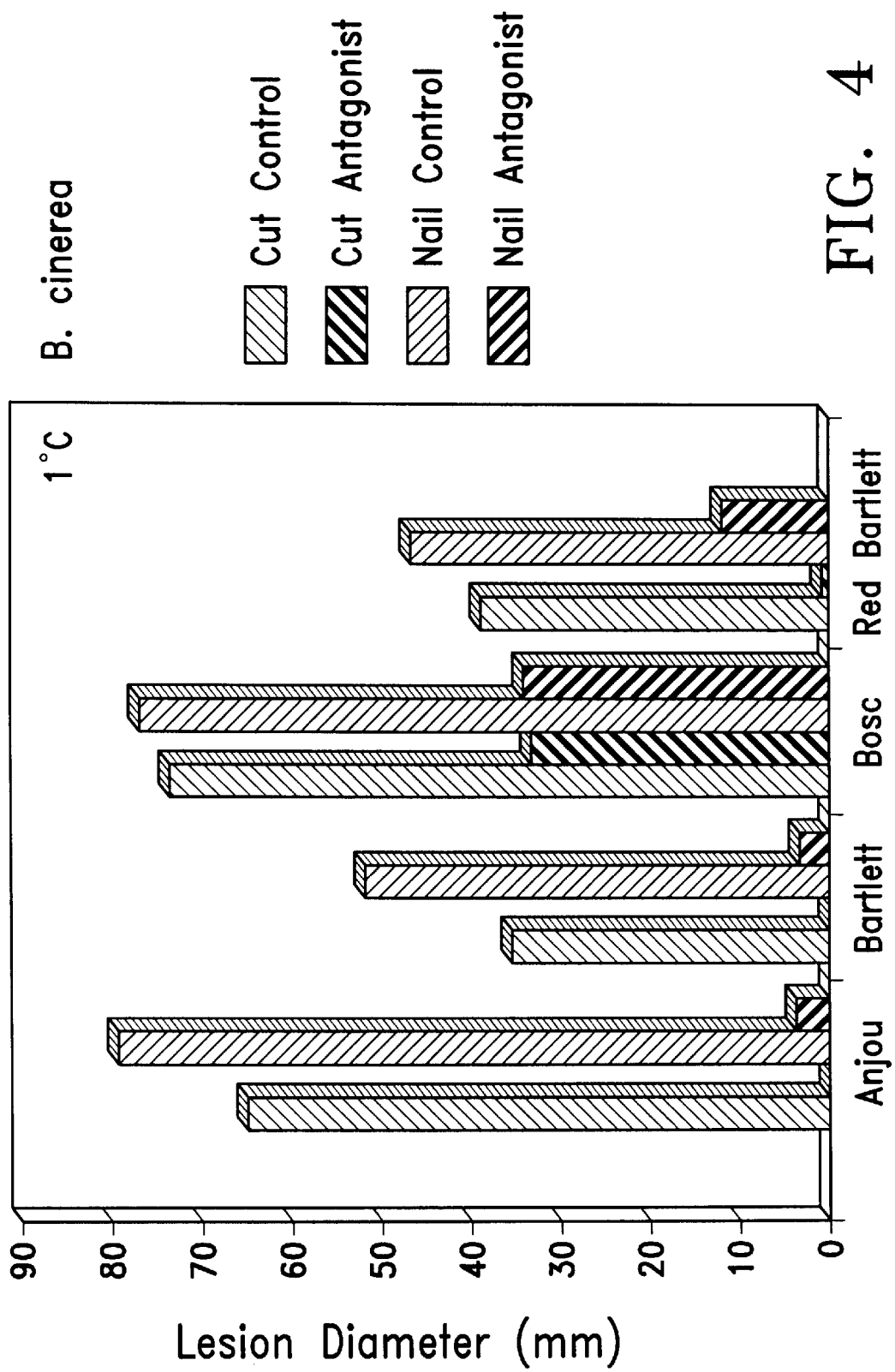
Figure 5:
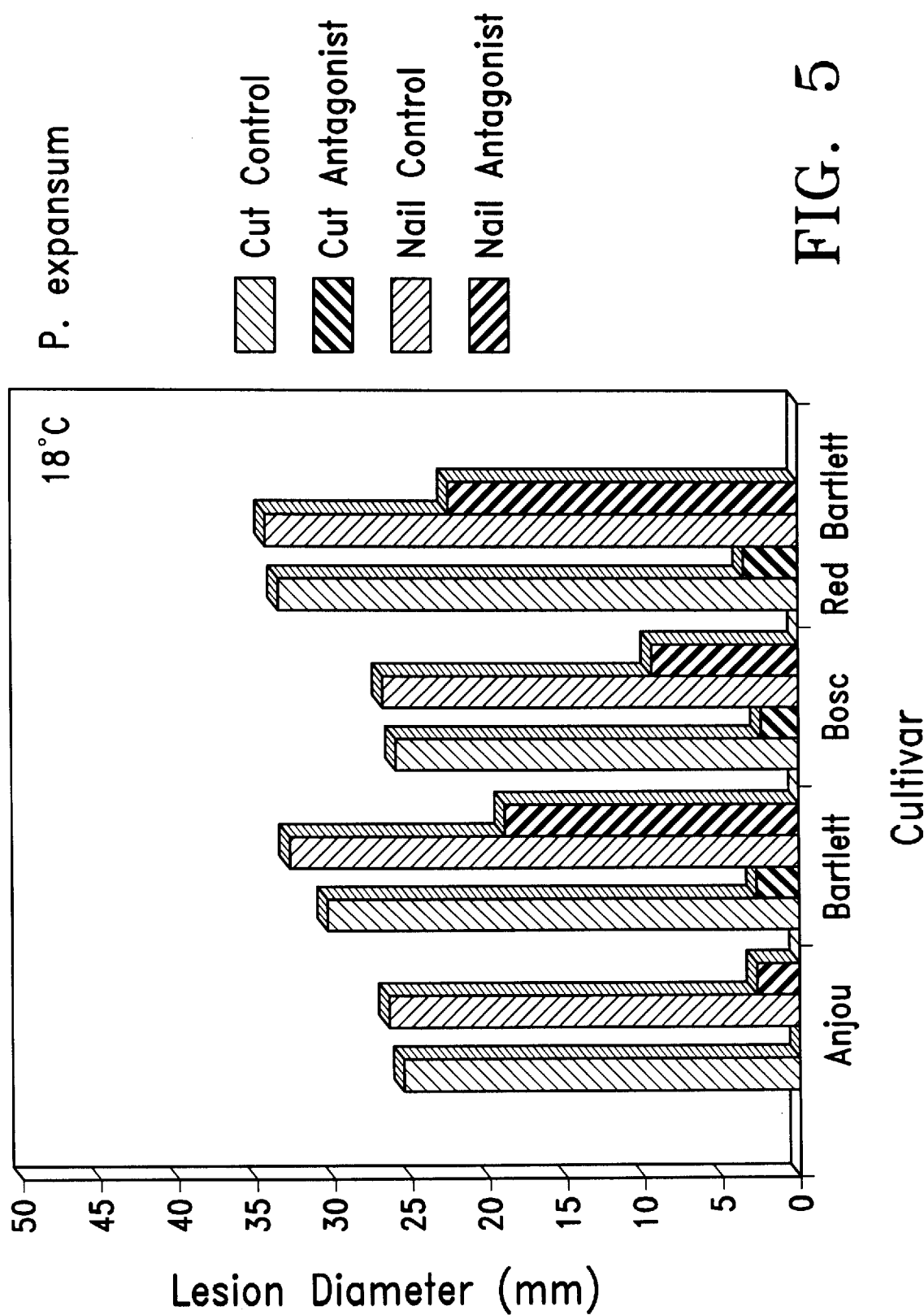
Figure 6:
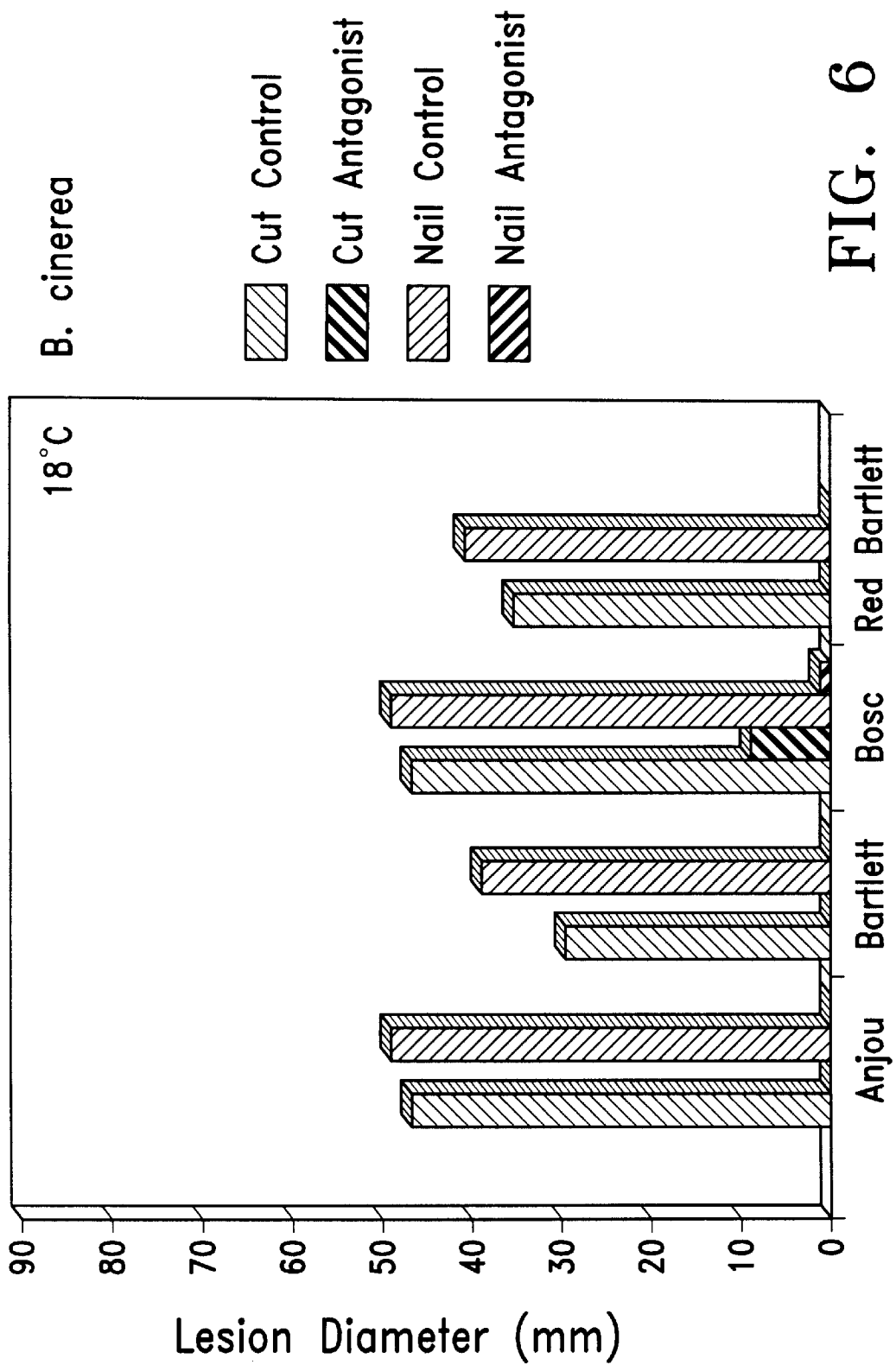

In two separate experiments, fruit were stored at 1° C. for 30 days (see FIGS. 3 and 4) and at 18° C. for 7 days (see FIGS. 5 and 6.

These results indicate that under simulated large scale storage conditions, *P. syringae* pv. *lachrymans* is effective at inhibiting postharvest disease.

It is envisioned that isolates of *P. syringae* pv. *lachrymans* particularly that of NRRL B-18739 having antifungal activity can be used to prevent or inhibit postharvest disease in other agricultural commodities prone to such disease.

There has been provided in accordance with the present invention strains of *P. syringae* pv. *lachrymans*, particularly isolate designated as NRRL B-18739 as well as methods of their use as biocontrol agents in the management of postharvest disease. It is envisioned and apparent that from the benefit of this disclosure, many alternatives and variations maybe practiced. The scope of the appended claims are intended to include all such alternatives and variations.

We claim:

1. A biological pure culture of *Pseudomonas syringae* pv. *lachrymans* having the distinguishing characteristics of the deposited strain designated as NRRL B-18739.

2. A biocontrol composition comprising:

*Pseudomonas syringae* pv. *lachrymans* having the distinguishing characteristics of the deposited strain designated NRRL B-18739 and an agriculturally acceptable excipient.

* * * * *